(12) United States Patent  
Takasu et al.

(10) Patent No.: US 8,835,474 B2  
(45) Date of Patent: *Sep. 16, 2014

(54) REMEDY FOR OVERACTIVE BLADDER COMPRISING ACETIC ACID ANILIDE DERIVATIVE AS THE ACTIVE INGREDIENT

(75) Inventors: Toshiyuki Takasu, Tsukubamirai (JP); Shuichi Sato, Tsukuba (JP); Masashi Ukai, Tsukuba (JP); Tatsuya Maruyama, Tsuchiura (JP); Masayuki Shibasaki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/117,638

(22) Filed: May 27, 2011

(65) Prior Publication Data

US 2011/0230530 A1  Sep. 22, 2011

Related U.S. Application Data

(60) Division of application No. 12/333,357, filed on Dec. 12, 2008, now abandoned, which is a continuation of application No. 10/534,290, filed as application No. PCT/JP03/14065 on Nov. 4, 2003, now Pat. No. 7,750,029.

(30) Foreign Application Priority Data

Nov. 7, 2002 (JP) .................. 2002-323792

(51) Int. Cl.
*A61K 31/426* (2006.01)
*C07D 277/40* (2006.01)

(52) U.S. Cl.
CPC ............ *A61K 31/426* (2013.01); *C07D 277/40* (2013.01)

USPC .......................................................... 514/370

(58) Field of Classification Search
None
See application file for complete search history.

(56) References Cited

U.S. PATENT DOCUMENTS 6,069,176 A   5/2000   Tsuchiya et al.
6,204,285 B1  3/2001   Fabiano et al.
6,291,491 B1  9/2001   Weber et al.

(Continued)

FOREIGN PATENT DOCUMENTS

AU   715216 B2   1/2000
AU   731391 B2   3/2001

(Continued)

OTHER PUBLICATIONS

Chen et al. ("Prevalence and Correlation of Urinary Incontinence and Overactive Bladder in Taiwanese Women", Neurourology and Urodynamics 2003, 22, 109-117).*

(Continued)

*Primary Examiner* — Kortney L Klinkel
(74) *Attorney, Agent, or Firm* — Fitzpatrick, Cella, Harper & Scinto

(57) ABSTRACT

(R)-2-(2-aminothiazol-4-yl)-4'-[2-[(2-hydroxy-2-phenylethyl)amino]ethyl]acetic acid anilide or its salt shows a potent bladder relaxation effect in "isolated rat bladder smooth muscle relaxation test", dose-dependently lowers the contraction frequency of rhythmic bladder contractions in "rat rhythmic bladder contraction measurement test" and, moreover, prolongs the urination intervals in "urination functions measurement test on cyclophosphamide-induced overactive bladder model rat". Owing to these effects, the above compound is useful as a remedy for overactive bladder.

12 Claims, 3 Drawing Sheets

ANTAGONISM TEST TO CONTRACTION BY CARBACHOL

(56) References Cited

U.S. PATENT DOCUMENTS

| | | | |
|---|---|---|---|
| 6,346,532 | B1 | 2/2002 | Maruyama et al. |
| 6,353,025 | B1 | 3/2002 | Tamai et al. |
| 6,538,152 | B1 | 3/2003 | Tanaka et al. |
| 6,630,515 | B2 | 10/2003 | Cruz et al. |
| 6,696,489 | B1 | 2/2004 | Tamai |
| 6,699,860 | B2 | 3/2004 | Ladouceur et al. |
| 6,790,865 | B2 | 9/2004 | Muranaka et al. |
| 7,342,117 | B2 | 3/2008 | Kawazoe et al. |
| 2003/0018061 | A1 | 1/2003 | Ogawa et al. |
| 2003/0073846 | A1 | 4/2003 | Taniguchi et al. |
| 2005/0004190 | A1 | 1/2005 | Kawazoe et al. |
| 2005/0014190 | A1 | 1/2005 | Blumenfeld et al. |
| 2008/0009538 | A1 | 1/2008 | Skolnick |
| 2008/0214633 | A1 | 9/2008 | Kawazoe et al. |

FOREIGN PATENT DOCUMENTS

| | | |
|---|---|---|
| EP | 0 420 120 A2 | 9/1990 |
| EP | 0958835 A1 | 11/1999 |
| EP | 1258253 A1 | 11/2002 |
| EP | 1028111 B | 5/2004 |
| GB | 2356197 A | 5/2001 |
| JP | 06-293664 A | 10/1994 |
| JP | 07-228543 A | 8/1995 |
| JP | 2001-114736 A1 | 4/2001 |
| WO | 92/18461 A1 | 10/1992 |
| WO | 93/15041 A1 | 8/1993 |
| WO | 94/25427 A1 | 11/1994 |
| WO | 97/15549 A1 | 5/1997 |
| WO | 9807445 A1 | 2/1998 |
| WO | 9920607 A1 | 4/1999 |
| WO | 9931045 A1 | 6/1999 |
| WO | 9952856 A1 | 10/1999 |
| WO | 0002846 | 1/2000 |
| WO | 01/54728 A1 | 8/2001 |
| WO | 0162705 A2 | 8/2001 |
| WO | 0200622 A2 | 1/2002 |

OTHER PUBLICATIONS

Abrams, et al., "The Standardisation of Terminology in Lower Urinary Tract Function: Report From the Standardisation Sub-Committee of the International Continence Society", Urology (2003) pp. 37-49, vol. 61.

Abrams et al., "The Standardisation of Terminology in Lower Urinary Tract Function: Report From the Standardisation Sub-Committee of the International Continence Society," Neurourology and Urodynamics, 21:167-178 (2002).

Andersen et al., "Abnormalities of Bladder Innervation in Diabetes Mellitus", Urology, 7(4):442-448 (1976).

Blin et al, "Structural and Conformational Features Determining Selective Signal Transduction in the Beta3-Adrenergic Receptor", The American Society for Pharmacology and Experimental Therapeutics, 44:1094-1104 (1993).

Canadian Office Action issued in Application No. 2503570, dated Jun. 14, 2010.

Cecil Textbook of Medicine, 1:23-24 and 637-642 (2000).

Elliot et al., Mayo Clin Proc., 76:353-355 (2001).

Howe, "Beta-Adrenergic Agonists", Drugs of the Future, 18(6):529-549 (1993).

Igawa et al, "Relaxant Effects of Isoproterenol and Selective Beta-3Adreenoceptor Agonists on Normal Low Compliant and Hyperreflexic Human Bladders", The Journal of Urology, 165:240-244 (2001).

Igawa et al, The Japanese Journal of Urology, 88(2):183 (1997).

Korean Office Action issued in Appl No. 10-2005-7008158, dated Nov. 21, 2009.

Longhurst et al., "Pharmacological characterization of Beta-adrenoceptors mediating relations of the rat urinary bladder in vitro", British Journal of Pharmacology, 127:1744-1750 (1999).

Michel et al., "Effect of Diabetes on Lower Urinary Tract Symptoms in Patients with Benign Prostatic Hyperplasia", Journal of Urology, 163(6):1725-1729 (2000).

Morita et al, The Japanese Journal of Urology, 88(2):119 (1997).

Morita et al., "Function and Distribution of Beta-sub3-Adrenoceptors in Rat, Rabbit and Human Urinary Bladder and External Urethral Sphincter", J. Smooth Muscle Res., 36:21-32 (2000).

Osamu Yamaguchi; "β3-Adrenoceptors in Human Detrusor Muscle"; Elsevier Science Inc.; May 2002, Urology 59 (Supplement 5A); pp. 25-29.

Polish Office Action issued in Application No. P-376771 dated Mar. 31, 2011.

Wagner et al., "Health-Related consequences of overactive bladder", The American Journal of Managed Care, 8(19, Supp.):S598-607 (2002).

Weiss et al., "Nocturia", Journal of Urology, 163(1):5-12 (2000).

World Health Organization, Definition and Diagnosis of Diabetes Mellitus and Intermediate Hyperglycemia, WHO/IDF Consultation (2006).

World Health Organization, Definition, Diagnosis and Classification of Diabetes Mellitus and its Complications, WHO (1999).

Zhao et al, "Advances on the Research on and Development of Beta-sub3-Adrenoceptors Agonists", Chinese Journal of Medicinal Chemistry, 11(3):177-181 (2001).

Myrbetriq® Package Insert (Jun. 28, 2012).

Tatsuya Maruyama, "Discovery of YM178 (Mirabegron) as a Potent and Selective β3 Adrenoceptor Agonist for the Treatment of Overactive Bladder", Drug Discovery Research, Astellas Pharma Inc. (2012).

Cecchi, R., et al., "Synthesis and β-adrenergic activity of atypical β-adrenergic phenylethanolaminotetralin steroisomers", Eur. J. Med. Chem. (1994) 29, 259-267.

Arch, JRS, "β-3 and Atypical β-adrenoceptors", Medical Research Reviews, vol. 13, No. 6, 663-729 (1993).

Larsen, J-J, "α and β-Adrenoceptors in the Detrusor Muscle and Bladder Base of the Pig and β-Adrenoceptors in the Detrusor Muscle of a Man". British Journal of Pharmacology, 1979, vol. 65, p. 215-222.

Hattori K., et al., "Asymetric Synthesis of FR165914; Novel β-3-Adrenerigic Agent with a Benzocycloheptene Structure", Bioranic & Medicinal Chemistry Letters, vol. 5, No. 23, pp. 2821-2824 (1995).

Kuratani, K., et al., "Enhancement of Gastric Mucosal Blood Flow by Beta-3 Adrenergic Agonists Prevents Indomethacin-Induced Antral Ulcer in the Rat", The Journal of Pharmacology and Experimental Therapeutics, (1994), vol. 270, No. 2, p. 559-565.

"Fujisawa synthesizes novel beta 3-agonist", The Prous Science Daily Essentials, May 3, 1996.

Nergardh, et al., "Characterization of the Adrenergic Beta-Receptor in the Urinary Bladder of Man and Car", Acta pharmacol. et toxicol. 1977, 40, 14-21.

Bianchetti, A., et al., "In vitro inhibition of intestinal motility by phenylethanolaminotetralines; evidence of atypical β-adrenoceptors in rat colour", Br. J. Pharmacol. (1990) 100, 831-839.

Sacco, E., et al., "Mirabegron: a review of recent data and its prospects in the management of overactive bladder", Therapeutic Advances in Urology, (2012) 4(6) 315-324.

Bylund, D., et al., "IV. International Union of Pharmacology Nomenclature of Adrenoceptors" Pharmacological Reviews, 1994, vol. 46, No. 2 p. 121-136.

English translation of Written Demand for Trial (Mar. 24, 2011), filed in the Japanese Patent Office on Kissei Patent No. 4685201.

English translation of Written Statement (1) (Sep. 30, 2011), filed in the Japanese Patent Office on Kissei Patent No. 2011-800046.

English translation of Written Oral Argument Statement Summary (Nov. 2, 2011), filed in the Japanese Patent Office on Kissei Patent No. 2011-800046.

Israeli Office Action in Israeli Patent Application No. 168121 dated Jul. 2, 2009.

Canadian Office Action issued in Application No. 2,503,570, dated Dec. 14, 2009.

Chinese Office Action in Chinese Application No. 2003801012899.4 dated Nov. 10, 2006.

Notice of Filing and Particulars of Grounds of Invalidity regarding Kissei Australian Patent No. 731391, filed in the Federal Court of Australia, dated Mar. 2, 2010.

(56) References Cited

OTHER PUBLICATIONS

"International Preliminary Report on Patentability" in Application No. PCT/JP2003/014065 dated May 26, 2004.
Supplementary European Search Report in European Application No. 03770134.9 dated Apr. 19, 2007.
Badone B., et al., "Synthesis of the Potent and Selective Atypical β-adrenergic Agonist SR59062A", Biorganic & Medicinal Chemistry Letters, vol. 4. No. 16, pp. 1921-1924 (1994).
Johnson M., "The β-Adrenoceptor" American Journal of Respiratory and Critical Care Medicine, vol. 158, pp. S146-S153 (1998).
Krief S., et al. "Tissue Distribution of β3-adrenergic Receptor mRNA in Man" Journal of Clinical Investigation, vol. 91, pp. 344-349 (1993).
Takeda H., et al. "Functional Characterization of β-Adrenoceptor Subtypes in the Canine and Rat Lower Urinary Tract" The Journal of Urology, vol. 170, pp. 654-658 (2003).
You-Tang S., et al. "Peripheral Vascular Effects of Beta-3 Adrenergic Receptor Stimulation in Conscious Dogs" The Journal of Pharmacology and Experimental Therapeutics, vol. 268, pp. 466-473 (1994).
Emorine, L., et al., "The human β3-adrenoceptor: the search for a physiological function", TiPS, vol. 15, pp. 3-7 (1994).
Hegde SS, "Muscarinic receptors in the bladder: from basic research to therapeutics" British Journal of Pharmacology, vol. 147, pp. S80-587 (2006).
You-Tang S., et al. "Differences in β3-Adrenergic Receptor Cardiovascular Regulation in Conscious Primates, Rats and Dogs" The Journal of Pharmacology and Experimental Therapeutics, vol. 278, pp. 1435-1443 (1996).
Takeda H., et al. "Role of the β3-Adrenoceptor in Urine Storage in the Rat: Comparison between the Selective β3-Adrenoceptor Agonist, CL316.243, and Various Smooth Muscle Relaxants" The Journal of Pharmacology and Experimental Therapeutics, vol. 293, pp. 939-945 (2000).
Hammond TG, et al. "Methods of collecting and evaluating nonclinical cardiac electrophysiology data in the pharmaceutical industry: results of an international survey" Cardiocascular Research, vol. 49, pp. 741-750 (2001).
Weyer C., et al. "Increase in Insulin Action and Fat Oxidation After Treatment With CL 316,243, a Highly Selective β3-Adrenoceptor Agonist in Humans" Diabetes, vol. 47, pp. 1555-1561 (1998).
Ishiura Y., "Experimental Study of Voiding Dysfunction Induced by Cerebral Infraction in Rats" Nihon Hinyoki-gakkaishi, vol. 87, pp. 1221-1230 (1996).
Anthony A., Localization of the β (beta) 3-adrenoceptor in the human gastrointestinal tracts: an immunohistochemical study Aliment Pharmacol. Ther., vol. 12, pp. 519-525 (1998).
Myslivecek, et al. "Distrubution of mRNA and binding sites of adrenocreptors and muscarinic receptors in the rat heart" Life Sciences (2005) Life Sciences (2005).
Yamaguchi O., "Pharmacological of Treatment of Overactive Bladder" Pharma Medica, vol. 24, pp. 37-40 (2006).
Moniotte S., et al. "Real-time RT-PCR for the Detection of Beta-adrenoceptor Messenger RNAs in Small Human Endomyocardial Biopsies" J Mol. Cell Cardiol., vol. 33, pp. 2121-2133 (2001).
Chamberlain PD, "The tissue distribution of the human β3-adrenoceptor studied using a monoclonal antibody: Direct evidence of the β3-adrenoceptor in human adipose tissue, atrium and skeletal muscle" International Journal of Obesity, vol. 23, pp. 1057-1065 (1999).
Matteis RD, let al. "Immunohistochemical identification of the β3-adrenoceptor in intact human adipocytes and ventricular myocardium: effect of obesity and treatment with ephedrine and caffeine" nternational Journal of Obesity, vol. 26, pp. 1442-1450 (2002).
Li JH, et al. "β-Adrenoceptor Subtypes in the Detrusor of Guinea-Pig Urinary Bladder" Pharmacology, vol. 44, pp. 13-18 (1992).
Seguchi H, et al. "Expression of beta 3-Adrenoceptors in Rat Detrusor Smooth Muscle" The Journal of Urology, vol. 159, pp. 2197-2201 (1998).
Forrest MJ, et al. "L-750355, a human β3-adrenoceptor agonist; in vitro pharmacology and profile of activity in vivo in the rhesus monkey" European Journal of Pharmacology, vol. 407, pp. 175-181 (2000).
Levin, RM., et al. "Identification of Receptor Subtypes in the Rabbit and Human Urinary Bladder by Selective Radio-Ligand Binding" The Journal of Urology, vol. 139, pp. 844-848 (1988).
Hutchinson DS, et al. "Mouse β3a and βb-adrenoceptors expressed in Chinese hamster ovary cells display identical pharmacology but utilize distinct signalling pathways" British Journal of Pharmacology, vol. 135, pp. 1903-1914 (2002).
Evans BA, et al. "Alternative splicing generates two isoforms of the β3-adrenoceptor which are differentially expressed in mouse tissues" British Journal of Pharmacology, vol. 127, pp. 1525-1531 (1999).
Yamamoto Y., et al. "The Effects of β-Adrenoceptor Agonists on KCI-induced Rhythmic Contraction in the Ureter of Guinea Pig" Journal of Smooth Muscle Research, vol. 36, pp. 13-19 (2000).
Oshita M., et al. "Characterization of β-adrenoceptors in urinary bladder: comparison between rat and rabbit" British Journal of Pharmacology, vol. 122, pp. 1720-1724 (1997).
Kubota Y., et al. "Inhibitory mechanism of BRL37344 on muscarinic receptor-mediated contractions of the rat urinary bladder smooth muscle" Naunyn-Schmiedeberg's Arch Pharmacol., vol. 366, pp. 198-203 (2002).
Bardou M., et al. "In vitro inhibition of human colonic motility with SR 59119A and SR 59104A: evidence of a β3-adrenoceptor-mediated effect"European Journal of Pharmacology. vol. 353, pp. 281-287 (1998).
Yono M., et al. "Pharmacological effects of tolterodine on human isolated urinary bladder" European Journal of Pharmacology, vol. 368, pp. 223-230 (1999).
Yoshida M., et al. "Age-related changes in cholinergic and purinergic neurotransmission in human isolated bladder smooth muscles" Expermental Gerontology, vol. 36, pp. 99-109 (2001).
Ozawa H., et al. "Effect of Intravesical Nitric Oxide Therapy on Cyclophosphamide-Induced Cystitis" The Journal of Urology, vol. 162, pp. 2211-2216 (1999).
Alfieri AB, et al. "Nlitric oxide synthases and cyclophosphamide-induced cystitis in rats" Naunyn-Schmiedeberg's Arch Pharmacol., vol. 363, pp. 353-357 (2001).
Lecci A., et al. "Pharmacological evaluation of the role of cyclooxygenase isoenzymes on the micturition reflex following cystitis in rats" British Journal of Pharmacology, vol. 130, pp. 331-338 (2000).
Yanagisawa T., et al., "Selectivity and Potency of Agonists for the Three Subtypes of Cloned Human β-adrenoceptors Expressed in Chinese Hamster Ovary Cells", Tohoku J Exp. Med., vol. 192, pp. 181-193 (2000).
Kato T., et al., "Synthesis of a New β3-Selective Adrenergic Receptor Agonist, FR149175" Nihon Yakugakukai 116th annual meeting (1996), p. 261.
Lipworth BJ, "Clinical pharmacology of β3-adrenoceptors" British Journal of Pharmacology, vol. 42, pp. 291-300 (1996).
Liu S., et al., "Effects of Atropine, Isoproterenol and Propranolol on the Rabbit Bladder Contraction Induced by Intra-Arterial Administration of Acetylcholine and ATP" The Journal of Urology, vol. 160, pp. 1863-1866 (1998).
Growcott UW, "Zeneca ZD7114 acts as an antagonist at β3-adrenoceptors in rat isolated ileum" British Journal of Pharmacology, vol. 110, pp. 1375-1380 (1993)Growcott UW, British Journal of Pharmacology, vol. 110, pp. 1375-1380 (1993).
Park Y., "Existence of β3-Adrenoceptor and it's Functional Roll in the Human Ureter" The Journal of Urology, vol. 157, p. 77 (1997).
J. Mysliveček, J. Říčný, S. Tuček, "Muscarinic and β-adrenergic receptors in rat heart during hydrocortisone treatment", Life Sciences, vol. 64, Issues 6-7, pp. 355-596 (Jan. 8, 1999).
Igawa Y., et al., "Functional and Molecular Biological Evidence of β3 Adrenoceptors in the Human Detrusor" The Journal of Urology, vol. 157, p. 175, No. 4 Supplmental Apr. 14, 1997.
Yamasaki Y., et al., "β-Adrenalin Receptor Subtype in the Rabbit, Rat, and Dog Bladder Detrusor Muscle" (1997) 85th annual meeting of Japanese Urological Association, The Japanese Journal of Urology, vol. 88, p. 119 (183) (1997).

(56) References Cited

OTHER PUBLICATIONS

Takeda M., et al., "Expression of β-Adrenergic Receptor Subtype mRNA and β-Adrenergic Receptor Kinase mRNA in the Human Bladder Detrusor Muscle—The Role of β-Adrenergic Receptors in Urine Collection and the Possibility of the Presence of a Desensitization Mechanism" (1997) 85th annual meeting of Japanese Urological Association, The Japanese Journal of Urology, vol. 88, p. 119 (183) (1997).
Park Y., et al., "β-Adrenaline Receptor Subtypes in the Human Ureter" (1997) 85th annual meeting of Japanese Urological Association, The Japanese Journal of Urology, vol. 88, p. 152 (216) (1997).
Seguchi H., et al., "β3-Adrenaline Receptor Expression in Rat Bladder" (1997) 85th annual meeting of Japanese Urological Association, The Japanese Journal of Urology, vol. 88, p. 230 (294) (1997).
Toyama M., et al., "Species Differences in β-Adrenaline Receptor Subtypes in the Ureteral Smooth Muscle" (1997) 85th annual meeting of Japanese Urological Association, The Japanese Journal of Urology, vol. 88, pp. 235 (299) (1997).
Fabrizio DP, et al., "Functional Evidence for the Presence of βB-Adrenoceptors in the Guinea Pig Common Bile Duct and Colon" Pharmacology, vol. 51, pp. 288-297 (1995).
Galitzky J., et al. "Lipolytic effects of conventional β3-adrenoceptor agonists and of CGP 12,177 in rat and human fat cells: preliminary pharmacological evidence for a putative β4-adrenoceptor", British Journal of Pharmacology, vol. 122, pp. 1244-1250 (1997).
Yamaguchi O., et al., "Evaluation of mRNAs Encoding Muscarinic Receptor Subtypes in Human Detrusor Muscle" The Journal of Urology, vol. 156, pp. 1208-1213 (1996).
Kawashima H., et al. "A novel human beta-3 adrenoceptor agonist AD-9677", Oct. 22, 1997, p. 1469 16th International Diabetes Federation Congress.
Takeda M., "The Role of Autonomic Receptors and Neuroactive Substances in the Lower Urinary Tract Smooth Muscle Tissue" (Japanese), Apr. 8-11, 1998, 86th annual meeting of the Japanese Urological Association, pp. 19-20.
Morita T., et al. "The Effect of new beta-3 agonist, GC-332 to bladder function in anesthesia rats" (Japanese), Apr. 8-11, 1998, 86th annual meeting of the Japanese Urological Association.
Takeda H., et al. "Effects of β-Adrenaline Receptor Agonists on the Intravesical Pressure in Anesthetized Rats" Apr. 8-11, 1998, 86th annual meeting of the Japanese Urological Association, p. 49.
Takeda M., et al. "Adrenergic beta-1, beta-2 and beta-3 receptor subtypes in the detrusor of human urinary bladder—evaluation by mRNA expression and isometric contraction-", Apr. 13, 1997 92th annual meeting of American Urological Association, p. 82.
Yamazaki Y., et al. "Characterization of KUC-7483 and its active metabolite KUC-7322, a selective beta-3 adrenoceptor agonist on bladder function in rat" 32nd Annual Meeting of International Continence Society, p. 95 (2002).
Takeda M., et al. "β3 Receptor in the Human Bladder Detrusor Muscle-Molecular-biological and Pharmacological Study" Sep. 23, 1997 4th Japanese Neurogenic Bladder Association, p. 54.
Toyama M., et al. "β-Adrenaline Receptor Subtype in Rabbit and Dog Ureteral Smooth Muscle", Sep. 23, 1997 4th Japanese Neurogenic Bladder Association, p. 63.
Park Y., et al. "The Presence of β3-Adrenaline Receptors in the Human Ureter", Sep. 23, 1997 4th Japanese Neurogenic Bladder Association, p. 64.
Morita T., et al. "The Presence and Function of β3 Receptors in the Bladder and External Urethral Sphincter" (1997) 85th annual meeting of Japanese Urological Association, p. 119.
Igawa Y.,"Pharmacological and Molecular-biological Elucidation of β3-Adrenalin Receptor Function in the Human Detrusor Muscle" (1997) 85th annual meeting of Japanese Urological Association, p. 119.
Bloom, J., et al. Drugs of the Future, vol. 19, pp. 23-26 (1994).
Strosberg, D., et al. "Function and regulation of the β3-Adrenoceptpor" TIPS, vol. 17 pp. 373-381 (1996).
Manara, L., et al., "The phenylethanolaminotetralines: new selective agonists for atypical β-adrenoceptpor", TIPS, vol. 11, pp. 229-230 (1990).
Nomiya M., "mRNA Expression level of alpha-1 and beta adrenoceptor (AR) subtypes and their roles in human bladders", Apr. 20, p. 167 (2002).
Igawa Y., "Functional elucidation of beta-adrenoceptors in isolated human detrusor: Study using novel beta3-adrenoceptor agonist, KUC-7322" 9th annual meeting of Japanese voiding function association (2002).
Igawa Y., "Functional Investigation of beta adrenoceptor in isolated human detrusor—using novel selective beta-3 adrenoceptor agonist KUC-7322", 32nd Annual Meeting of International Continence Society (2002).
Arch JRS, et al. (1984) "Atypical β-adrenoceptors on brown adipocytes as a target for anti-obesity drugs" Nature (Lond) 309:163-165.
Berkowitz DE, et al. (1995) "Distribution of β-3-adrenoceptor mRNA in human tissues" Eur. J. Pharmacol. 289:223-228.
Daniels DV, al. et al (1999) "Functional pharmacological characterization of the muscarinic cholinoceptor-mediated inhibition of adenylyl cyclase in primary cultured human bladder detrusor smooth muscle cells" Life Sci. 64:590.
Dolan JA, et al. (1994) "β-3 Adrenoceptor selectivity of the dioxolane dicarboxylate phenethanolamines" J. Pharmacol. Exp. Ther. 269:1000-1006.
Emorine LJ, et al. (1989) Molecular characterization of the human β3-adrenergic receptor: Science (Wash DC) 245:1118-1121.
Frazier EP, et al. (2005) "Does cyclic AMP mediate rat urinary bladder relaxation by isoproterenol?" J. Pharmacol. Exp. Ther. 313:260-267.
Fujimura T. et al. (1999) "Expression and possible functional role of the β3-adrenoceptor in human and rat detrusor muscle" J. Urol. 161:680-685.
Furuno T. et al. (2006) "Enhanced inhibitory effects of beta-adrenoceptor agonist on cholinergic micturition contractions in muscarinic M2 receptor knockout mice" Neurourol. Urodyn. 25:590-591.
Granneman JG, et al. (1991) "Molecular cloning and expression of the rat β3-adrenergic receptor" Mol. Pharmacol. 40:895-899.
Hegde SS, et al. (1997) "Functional role of M2 and M3 muscarinic receptors in the urinary bladder of rats in vitro and in vivo" Br. J. Pharmacol. 120:1409-1418.
Hu B. et al. (2003) "Orally bioavailable beta 3-adrenergic receptor agonists as potential therapeutic agents for obesity and type-II diabetes" Prog. Med. Chem. 41:167-194.
Igawa Y. et al. (1998) "Possible β3-adrenoceptor-mediated relaxation of the human detrusor" Acta. Physiol. Scand. 164:117-118.
Igawa Y. et al. (1999) "Functional and molecular biological evidence for a possible β3-adrenoceptor in the human detrusor muscle" Br. J. Pharmacol. 126:819-825.
Igawa Y (2000) "Discussion: functional role of M1, M2, and M3 muscarinic receptors in overactive bladder" Urology 55:47-49.
Kaidoh K. et al. (2002) "Effects of selective β2 and β3-adrenoceptor agonists on detrusor hyperreflexia in conscious cerebral infracted rats" J. Urol. 168:1247-1252.
Langin D. et al. (1991) "Coexistence of three β-adrenoceptor subtypes in white fat cells of various mammalian species" Eur. J. Pharmacol. 199:291-301.
Liggett SB, (1992) "Functional properties of the rat and human β3-adrenergic receptors: differential agonist activation of recombinant receptors in Chinese hamster ovary cells" Mol. Pharmacol. 42:634-637.
Nahmias C. et al. (1991) "Molecular characterization of the mouse β3-adrenergic receptor: relationship with the atypical receptor of adipocytes" EMBO (Eur. Mol. Biol. Organ) J. 10:3721-3727.
Nomiya M. et al. (2003) "A quantitative analysis of mRNA expression of β1 and β-adrenoceptor subtypes and their functional roles in human normal and obstructed bladders" J. Urol. 170:649-653.
Takasu T. et al. (2007) "Effect of (R)-2-(2-Aminothiazol-4-yl)-4'-{2-[(2-hydroxy-2 phenylethyl)amino]ethyl} Acetanilide (YM178), a Novel Selective β3-Adrenoceptor Agonist, on Bladder Function," J. Pharmacol. Exp. Ther. 321(2):642-647.

(56) References Cited

OTHER PUBLICATIONS

Takeda M. et al. (1999) "Evidence for β3-adrenoceptor subtypes in relation of the human urinary bladder detrusor: analysis by molecular biological and pharmacological methods" J. Pharmacol. Exp. Ther. 288:1367-1373.

Takeda H. et al. (2002) "Effects of β3-adrenoceptor stimulation on prostaglandin E2-induced bladder hyperactivity and on the cardiovascular system in conscious rats" Neurourol. Urodyn. 21:558-565.

Wilson S. et al. (1996) "Agonist potency at the cloned human beta-3 adrenoceptor depends on receptor expression level and nature of assay" J. Pharmacol. Exp. Ther. 279:214-221.

Woods M. et al. (2001) "Efficacy of the β3-adrenergic receptor agonist CL-316243 on experimental bladder hyperreflexia and detrusor instability in the rat" J. Urol. 166:1142-1147.

Yamazaki Y. et al. (1998) "Species differences in the distribution of β-adrenoceptor subtypes in bladder smooth muscle" Br. J. Pharmacol. 124:593-599.

Yarker Ye et al. (1995) "Oxybuthynin. A review of its pharmacodynamic and pharmacokinetic properties, and its therapeutic use in detrusor instability" Drugs & Aging 6:243-262.

J. K. Badawi et al., "Relaxant Effects of β-Adrenergic Agonists on Porcine and Human Detrusor Muscle," 185(2) Acta Physiol. Scand. 151-159 (Sep. 2005).

Notice of Allowance in Reissue U.S. Appl. No. 13/542,308 (Feb. 14, 2014).

* cited by examiner

ANTAGONISM TEST TO CONTRACTION BY CARBACHOL

ANTAGONISM TEST TO CONTRACTION BY POTASSIUM CHLORIDE

REMEDY FOR OVERACTIVE BLADDER COMPRISING ACETIC ACID ANILIDE DERIVATIVE AS THE ACTIVE INGREDIENT

This is a Divisional of U.S. application Ser. No. 12/333,357, which is a Continuation of U.S. application Ser. No. 10/534,290, filed May 9, 2005, now U.S. Pat. No. 7,750,029; which is a 371 of PCT/JP03/14065, filed Nov. 4, 2003; the disclosure of each of which is hereby incorporated by reference.

TECHNICAL FIELD

This invention relates to a remedy for overactive bladder comprising (R)-2-(2-aminothiazol-4-yl)-4'-[2-[(2-hydroxy-2-phenylethyl)amino]ethyl]acetic acid anilide or a salt thereof as an active ingredient.

BACKGROUND ART

Bladder of mammals is under a dual control of autonomic nerve and detrusor relaxes via an adrenaline β receptor by stimulation of sympathetic nerve upon urination while, upon excretion of urine, it contracts via a muscarine receptor by stimulation of parasympathetic nerve. As a remedy for overactive bladder resulted when the dual control as such is unbalanced, anticholinergic agents such as propiverine hydrochloride and oxybutynin hydrochloride have been mostly used at present. However, there are intractable cases showing resistance to such compounds and there are side effects caused by anticholinergic agents such as urinary dysfunction and dry mouth and, therefore, it is the current status that satisfactory clinical results are not always achieved.

Further, as a result of increase in population of aged people in recent years, numbers of patients suffering from overactive bladder are increasing year by year and, in view of QOL (quality of life) of patients, there has been a brisk demand for the development of new drugs.

The present inventors reported in Example 41 of a pamphlet of International Laid-Open WO 99/20607 that (R)-2-(2-aminothiazol-4-yl)-4'-[2-[(2-hydroxy-2-phenylethyl)amino]-ethyl]acetic acid anilide dihydrochloride has both promotion action for insulin secretion and enhancing action for insulin sensitivity and further has anti-obese and anti-hyperlipemic actions whereby it is a useful compound for the treatment of diabetes mellitus but there is neither suggestion nor disclosure for the therapeutic use for overactive bladder (refer to Patent Document 1).

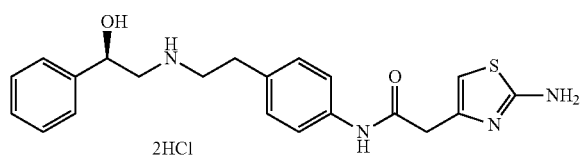 [SMILES: Nc1nc(CC(=O)Nc2ccc(CCNC[C@H](O)c3ccccc3)cc2)cs1]

In the meanwhile, in a pamphlet of International Laid-Open WO 98/07445, as an agent for prevention and treatment of urinary frequency and urinary incontinence containing a drug having stimulating action to a $\beta_3$-adrenaline receptor as an active ingredient, there is mentioned that CGP-12,177A represented by the following chemical structural formula has a relaxation action for bladder (refer to Patent Document 2). CGP-12,177A has been known as a selective drug having stimulating action to a $\beta_3$-adrenaline receptor (refer to Non-Patent Documents 1 and 2).

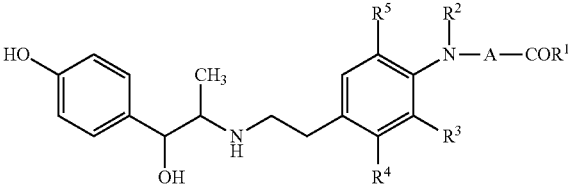

In a pamphlet of International Laid-Open WO 99/31045, compounds represented by the following formula are mentioned as having a stimulating action to a $\beta_3$-adrenaline receptor and as an agent for prevention or treatment of diseases caused by obesity, hyperglycemia and acceleration of movement of intestinal tract and diseases caused by urinary frequency or urinary incontinence, melancholia, biliary calculus or acceleration of bile duct movement (refer to Patent Document 3).

(In the formula, $R^1$ is hydroxyl group, a lower alkyl group, an aralkoxy group, amino group, etc.; $R^2$ is hydroxyl group or a lower alkyl group; $R^3$ is hydrogen atom or halogen atom; $R^4$ and $R^5$ each is hydrogen atom, halogen atom or a lower alkyl group; and A is a lower alkylene group.)

In a pamphlet of International Laid-Open WO 99/52856, compounds represented by the following formula are mentioned as having a stimulating action to a $\beta_3$-adrenaline receptor and as an agent for prevention or treatment of diseases caused by obesity, hyperglycemia and acceleration of movement of intestinal tract and diseases caused by urinary frequency or urinary incontinence, melancholia, biliary calculus or acceleration of bile duct movement (refer to Patent Document 4).

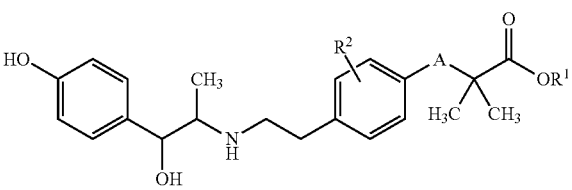

(In the formula, $R^1$ is hydrogen atom, a lower alkyl group or an aralkyl group; $R^2$ is hydrogen atom, a lower alkyl group or halogen atom; and A is oxygen atom or imino group.)

In a pamphlet of International Laid-Open WO 00/02846, compounds represented by the following formula are mentioned as having a stimulating action to a $\beta_3$-adrenaline receptor and as an agent for prevention or treatment of diseases caused by obesity, hyperglycemia and acceleration of movement of intestinal tract and diseases caused by urinary frequency or urinary incontinence, melancholia, biliary calculus or acceleration of bile duct movement (refer to Patent Document 5).

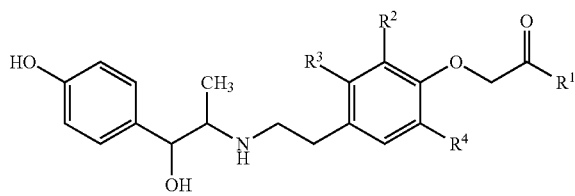

(In the formula, $R^1$ is hydroxyl group, etc.; one of $R^2$ and $R^3$ is hydrogen atom, halogen atom, etc. and another is hydrogen atom; and $R^4$ is halogen atom, etc.)

Patent Document 1: Pamphlet of International Laid-Open WO 99/20607
Patent Document 2: Pamphlet of International Laid-Open WO 98/07445
Patent Document 3: Pamphlet of International Laid-Open WO 99/31045
Patent Document 4: Pamphlet of International Laid-Open WO 99/52856
Patent Document 5: Pamphlet of International Laid-Open WO 00/02846
Non-Patent Document 1: *Drugs of the Future*, 1993, volume 18, no. 6, page 542
Non-Patent Document 2: *The American Society for Pharmacology and Experimental Therapeutics*, 1993, volume 44, page 1100

DISCLOSURE OF THE INVENTION

The present inventors have carried out intensive studies for finding new pharmacological effects of (R)-2-(2-aminothiazol-4-yl)-4'-[2-[(2-hydroxy-2-phenylethyl)amino]-ethyl] acetic acid anilide or a salt thereof (hereinafter, referred to as "the active ingredient of the present invention") which is useful as a remedy for diabetes mellitus and, as a result, they have found that the active ingredient of the present invention is useful as a remedy particularly for overactive bladder. In the present invention, overactive bladder is defined as a disease by which urinary urgency is frequently resulted. Although benign prostatic hyperplasia is exemplified as one of the causes for overactive bladder, there are many cases where the cause is ambiguous and they are called idiopathic overactive bladder. Although overactive bladder is sometimes accompanied by urinary frequency and urinary incontinence, it is not limited to the disease which is always accompanied by urinary frequency and urinary incontinence. Thus, in the case of mild overactive bladder, a patient is sensitive to the sense of wishing to urinate and frequently has a sense of wishing to urinate but, actually, he/she is able to hold his/her urine for a while. However, even in the case of a mild overactive bladder, its improvement has been strongly demanded in view of QOL (quality of life) of a patient. On the other hand, a severe overactive bladder is sometimes accompanied by urinary frequency and urinary incontinence. Urinary frequency is a state where number of times of urination is more than the normal one and is said to be not less than about two times at night and not less than about 8 times during 24 hours. In urinary incontinence, there is an involuntary leakage of urine and that is defined as a state where there is a problem socially or hygienically and is classified into stress urinary incontinence which occurs when abdominal pressure is applied such as cough and sneeze, urinary urge incontinence where a desire to urinate suddenly occurs and urine leaks before arriving at the toilet and urinary incontinence of a mixed type where both stress urinary incontinence and urinary urge incontinence are present.

The characteristic feature of the present invention is that the active ingredient of the present invention mitigates especially the frequent occurrence of urinary urgency of a patient and number of times of urination and state of urination are made into a more normal state. It goes without saying that overactive bladder in the present invention includes not only that as a result of benign prostatic hyperplasia but also that accompanied with urinary urgency, urinary incontinence and pollakiuria.

In Patent Document 1, the active ingredient of the present invention is useful, in addition to treatment of diabetes, as an agent for prevention and treatment of other diseases where an improvement in symptom is able to be achieved by reducing the symptom of obesity and hyperlipemia such as arteriosclerosis, ischemic cardiac disease such as cardiac infarction and angina pectoris, brain artery sclerosis such as cerebral infarction, aneurysm, etc. However, there is neither description nor suggestion at all to the effect that the active ingredient of the present invention is useful as a remedy for overactive bladder.

In Patent Document 2, use for overactive bladder is not mentioned as well. In Patent Document 2, there is a description that only CGP-12,177A has a relaxation action to bladder as a compound having a selective stimulating action to a $\beta_3$-adrenaline receptor. However, as compared with CGP-12, 177A, the active ingredient of the present invention has far stronger relaxation action for bladder. In addition, in Patent Document 2, there is no description for in vivo tests showing the usefulness for the treatment of overactive bladder such as "rat rhythmic bladder contraction measurement test" and "urination function measurement test on cyclophosphamide-induced overactive bladder model rat".

Further, use for overactive bladder is not mentioned in Patent Documents 3 to 5 as well. Compounds mentioned in Patent Documents 3 to 5 and the active ingredient of the present invention are different in their fundamental structures in such respects that the compounds mentioned in the documents always have a phenol ring but have no thiazole ring and also have no amide bond. In addition, in Patent Documents 3 to 5, there is no description for in vivo tests showing the usefulness for the treatment of overactive bladder such as "rat rhythmic bladder contraction measurement test" and "urination function measurement test on cyclophosphamide-induced overactive bladder model rat".

The present invention will now be illustrated in detail as hereunder.

In the present invention, (R)-2-(2-aminothiazol-4-yl)-4'-[2-[(2-hydroxy-2-phenylethyl)amino]ethyl]acetic acid anilide or a salt thereof is an active ingredient. The characteristic feature of the present invention is that the active ingredient of the present invention has been found to be useful as a remedy for overactive bladder which is a new use.

It is particularly preferred that the active ingredient of the present invention is a free base having no salt. However, it may form a salt with an acid and examples of the salt are acid addition salts with a mineral acid such as hydrochloric acid, hydrobromic acid, hydroiodic acid, sulfuric acid, nitric acid and phosphoric acid and an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid and glutamic acid. The active ingredient of the present invention having a salt may be easily manufactured from a free base by a common salt-forming reaction. The active ingredient of the present invention further includes hydrate, solvate and polymorphism. The active ingredient of the present invention still further includes pharmacologically acceptable prodrug. With regard to a group for forming the prodrug, that mentioned in *Prog. Med.* 5, 2157-2161 (1986) and "Iyakuhin no Kaihatsu" (Development of Drugs) (Hirokawa Shoten, 1990), volume 7, Molecule Design, 163-198 may be exemplified.

The drug containing the active ingredient of the present invention may be in any of forms of oral administration by tablets, pills, capsules, granules, diluted powder, etc. and parenteral administration by inhalant, etc. As to a solid composition for oral administration, tablets, diluted powder, granules, etc. are used. In the solid composition as such, one or more active ingredient(s) is/are mixed with at least one inert excipient such as lactose, mannitol, glucose, hydroxypropyl cellulose, microcrystalline cellulose, starch, polyvinylpyrrolidone and magnesium metasilicate aluminate. The composition may contain an inert additive such as lubricant (e.g., magnesium stearate), disintegrating agent (e.g., carboxymethyl starch sodium), solubilizing agent, etc. by a common method. Tablets and pills may, if necessary, be coated with sugar coat or with an intragastric or enteric coating agent. Dose may be appropriately decided for each case taking symptom, age and sex of the subject to be administered, etc. into consideration. Usually, it is about 0.01 mg/kg to 100 mg/kg per day for an adult in the case of oral administration and is administered either at one time or by dividing into two to four.

The active ingredient of the present invention is able to be easily manufactured by a method mentioned in Patent Document 1 but, since method for the manufacture of a free substance which is preferred as the active ingredient of the present invention is not specifically mentioned therein, such a manufacturing method is shown in Manufacturing Examples. Route for the manufacture is illustrated as follows.

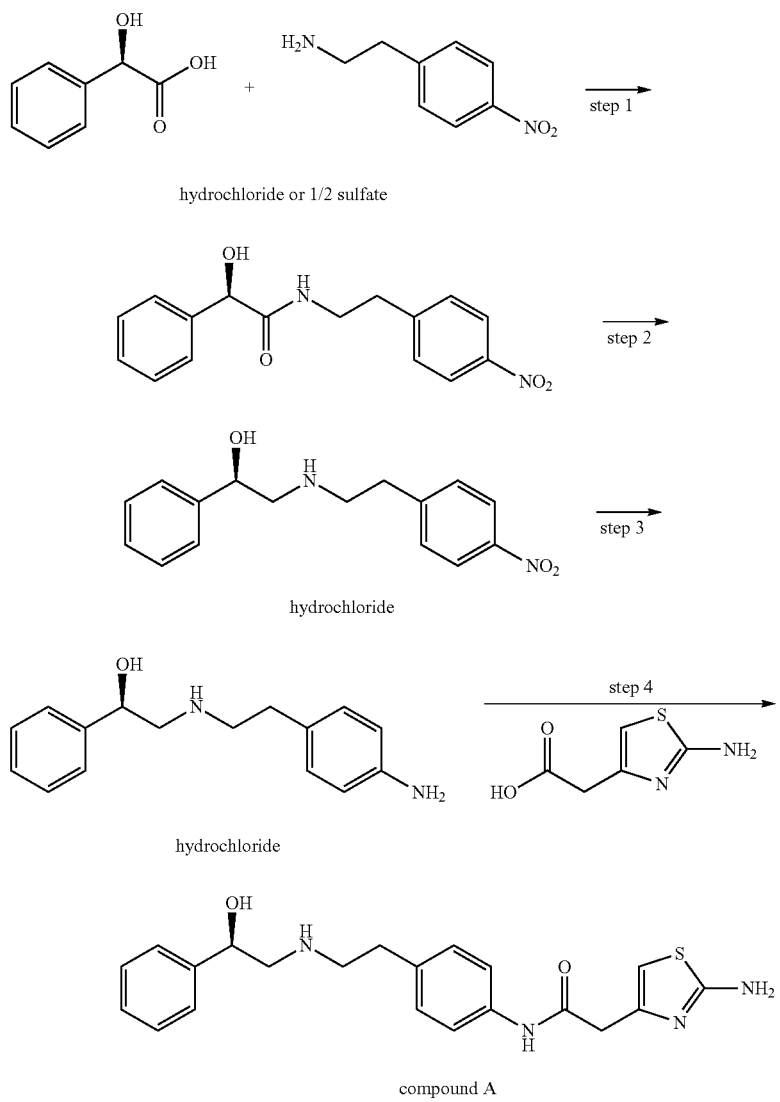

Manufacturing Examples

Manufacturing Method for the Active Ingredient of the Present Invention

Step 1

To a mixture of 5.90 kg of 4-nitrophenylethylamine monohydrochloride, 4.43 kg of (R)-mandelic acid, 2.94 kg of triethylamine and 22 liters of N,N-dimethylformamide were added 3.93 kg of hydroxybenztriazole and 5.58 kg of 1-(3-dimethylaminopropyl)-3-ethylcarbodiimide monohydrochloride (EDC) followed by stirring at about room temperature for 2 hours. EDC (0.28 kg) was further added thereto and the mixture was stirred at about room temperature throughout one night. The reaction solution was diluted with 110 liters of water and extracted with ethyl acetate (60 liters, 30 liters). The organic layer was successively washed with 60 liters of 1 M aqueous hydrochloric acid, 60 liters of 20% aqueous solution of potassium carbonate and water (60 liters, 60 liters) and concentrated in vacuo at 10 to 19° C. The residue was dissolved in 35 liters of toluene with heating at 87° C., cooled and stirred at 20° C. throughout one night. The resulting crystals were filtered and washed with 10 liters of toluene. This was dried in vacuo to give 7.66 kg of (R)-2-hydroxy-N-[2-(4-nitrophenyl)ethyl]-2-phenylacetamide as light yellow crystals.

$^1$H-NMR (DMSO-$d_6$, 400 MHz) δ (ppm)=2.87 (2H, t, J=7.2 Hz), 3.30-3.46 (2H, m), 4.85 (1H, d, J=4.8 Hz), 6.12 (1H, d, J=4.8 Hz), 7.20-7.33 (5H, m), 7.40 (2H, d, J=8.0 Hz), 8.04-8.12 (3H, m). FAB-MS m/z: 301 (M+H)$^+$.

Step 2

A mixture of 7.51 kg of (R)-2-hydroxy-N-[2-(4-nitrophenyl)ethyl]-2-phenylacetamide, 23 liters of 1,3-dimethyl-2-imidazolidinone and 23 liters of tetrahydrofuran was cooled at −18° C. and 49.4 kg of 1 M boran-tetrahydrofuran solution was dropped thereinto at not higher than −7° C. After that, temperature of the mixture was raised to 70° C. followed by stirring for 5 hours. The reaction mixture was cooled at −12° C. and 2.9 kg of methanol and 5.9 kg of concentrated hydrochloric acid were added thereto at not higher than 5° C. After stirring at 68° C. for 1 hour, the mixture was concentrated in vacuo until the amount became 50 liters. A 30% aqueous solution (60 kg) of $K_2CO_3$ and 6 liters of water were added thereto followed by extracting with 75 liters of ethyl acetate. The organic layer was washed with 75 liters of water and concentrated in vacuo. Isopropanol (75 liters) was added to the residue, the mixture was dissolved at 40° C. and 2.46 kg of concentrated hydrochloric acid was added to crystallize followed by stirring at 23° C. throughout one night. The crystals were filtered and washed with 38 liters of isopropanol. They were dried in vacuo to give 7.29 kg of (R)-2-[[2-(4-nitrophenyl)ethyl]amino]-1-phenylethanol monohydrochloride.

$^1$H-NMR (DMSO-$d_6$, 400 MHz) δ (ppm)=3.00-3.08 (1H, m), 3.15-3.30 (5H, m), 5.00-5.05 (1H, m), 6.23 (1H, d, J=4.0 Hz), 7.29-7.35 (1H, m), 7.36-7.43 (4H, m), 7.57 (2H, d, J=8.4 Hz), 8.21 (2H, d, J=8.4 Hz), 9.12 (2H, br). FAB-MS m/z: 287 (M+H)$^+$.

Step 3

A mixture of 11.0 kg of (R)-2-[[2-(4-nitrophenyl)ethyl]amino]-1-phenylethanol monohydrochloride, 110 liters of methanol and 1.20 kg of wet 10% palladium-carbon (wetting rate: 54.2%) was stirred in a hydrogen atmosphere until absorption of hydrogen stopped. The reaction solution was filtered and the filtrate was concentrated in vacuo. Methanol (40 liters) was added to the residue to dissolve at 40° C. and crystallization was conducted by addition of 220 liters of diisopropyl ether thereto followed by stirring at 20° C. throughout one night. The crystals were filtered and washed with 30 liters of diisopropyl ether. They were dried in vacuo to give 9.43 kg of (R)-2-[[2-(4-aminophenyl)ethyl]amino]-1-phenylethanol monohydrochloride.

$^1$H-NMR (DMSO-$d_6$, 400 MHz) δ (ppm)=2.76-2.90 (2H, m), 2.95-3.16 (4H, m), 4.95-5.11 (3H, m), 6.20 (1H, d, J=4.0 Hz), 6.53 (2H, d, J=8.4 Hz), 6.89 (2H, d, J=8.4 Hz), 7.28-7.43 (5H, m), 8.97 (1H, br), 9.29 (1H, br). FAB-MS m/z: 257 (M+H)$^+$.

Step 4

1-(3-Dimethylaminopropyl)-3-ethylcarbodiimide monohydrochloride (EDC) (5.76 g) was added to a mixture of 8.00 g of (R)-2-[[2-(4-aminophenyl)ethyl]amino]-1-phenylethanol monohydrochloride, 4.32 g of 2-aminothiazol-4-yl acetic acid, 2.64 g of concentrated hydrochloric acid and 120 ml of water at room temperature followed by stirring for 1 hour. A mixed solution of 2.40 g of sodium hydroxide and 40 ml of water was dropped into the reaction solution to crystallize. The resulting crystals were filtered, washed with water and dried in vacuo to give 9.93 g of (R)-2-(2-aminothiazol-4-yl)-4'-[2-[(2-hydroxy-2-phenylethyl)amino]-ethyl]acetic acid anilide (hereinafter, referred to as "compound A").

$^1$H-NMR (DMSO-$d_6$, 500 MHz) δ (ppm)=1.60 (1H, s), 2.59-2.66 (4H, m), 2.68-2.80 (2H, m), 3.45 (2H, s), 4.59 (1H, br), 5.21 (1H, br), 6.30 (1H, s), 6.89 (2H, s), 7.11 (2H, d, J=8.5 Hz), 7.19-7.23 (1H, m), 7.27-7.33 (4H, m), 7.49 (2H, d, J=8.5 Hz), 9.99 (1H, s). FAB-MS m/z: 397 (M+H)$^+$.

BEST MODE FOR CARRYING OUT THE INVENTION

The present invention will now be specifically illustrated by way of the following Examples but the present invention is not limited to the content thereof.

Example 1

Isolated Rat Bladder Smooth Muscle Relaxation Test

Test Method

The test was conducted by referring to *The Journal of Urology*, 1999, volume 161, page 680.

Male rats of Wistar strain of 10 to 11 weeks age were sacrificed by depletion, whole bladder was isolated by laparotomy and bladder sections each being in a size of about 3×10 mm were prepared in a nutrient solution which was well oxygenated with 95% $O_2$ and 5% $CO_2$ (Krebs-Henseleit solution (118.4 mM NaCl, 4.7 mM KCl, 1.2 mM $KH_2PO_4$; 1.2 mM $MgSO_4$, 2.5 mM $CaCl_2$, 25.0 mM $NaHCO_3$ and 11.1 mM glucose)). The section was hung in a Magnus tube in which a nutrient solution (Krebs-Henseleit solution) of 37° C. into which 95% $O_2$ and 5% $CO_2$ were aerated, stabilized for 30 to 60 minutes with a load of 1 g and $10^{-6}$ M carbachol (CCh) or 40 mM potassium chloride (KCl) was repeatedly applied thereto whereupon it was confirmed that reactivity to CCh or KCl became almost constant. After contraction by $10^{-6}$ M CCh or 40 mM KCl was induced and the generated tension was stabilized, a test drug (compound A or CGP-12, 177A) was cumulatively administered in 10-fold ratio with intervals of about 10 minutes and the relaxation reaction was observed. After completion of observation of relaxation reaction at maximum concentration of the test drug, $10^{-4}$ M papaverine was added to induce the maximum relaxation and a relaxation rate was calculated where the relaxation reaction was defined as 100%.

Results

As a result of the above test, the compound A which is the active ingredient of the present invention showed a strong relaxation action in antagonism test to contraction by carbachol and antagonism test to contraction by potassium chloride in an isolated rat bladder smooth muscle relaxation test. In addition, the compound A showed a significantly strong relaxation action as compared with CGP-12,177A (control compound).

Relaxation rates to drug concentration of the compound A which is the active ingredient of the present invention and the control compound are shown in FIG. 1 (antagonism test to contraction by carbachol) and FIG. 2 (antagonism test to contraction by potassium chloride), respectively. Further, $EC_{50}$ and maximum relaxation rate of the test drug in the antagonism test to contraction by carbachol are shown in Table 1 while concentration comparison of the compound A expressing the maximum relaxation rate of CGP-12,177A is shown in Table 2. The compound A showed an action strength of 270-fold as compared with the CGP-12,177A (control compound). Similarly, $EC_{50}$ and maximum relaxation rate of the test drug in the antagonism test to contraction by potassium chloride are shown in Table 3 while concentration comparison of the compound A expressing the maximum relaxation rate of CGP-12,177A is shown in Table 4. The compound A showed an action strength of 383-fold as compared with the CGP-12,177A (control compound).

TABLE 1

$EC_{50}$ and maximum relaxation rate of the test drug in the antagonism test to contraction by carbachol

| Test Drug | $EC_{50}$ (M) | Maximum Relaxation Rate (%) |
|---|---|---|
| Compound A (Active Ingredient of the Present Invention) | $5.2 \times 10^{-6}$ | 94.0 |
| CGP-12, 177A (Control Compound) | $>10^{-4}$ | 15.7 |

TABLE 2

Concentration comparison of the compound A expressing the maximum relaxation rate of CGP-12, 177A in antagonism test to contraction by carbachol

| Test Drug | Concentration (M) | Comparison of Action Strength* |
|---|---|---|
| Compound A (Active Ingredient of the Present Invention) | $3.7 \times 10^{-7}$ | 270 |
| CGP-12, 177A (Control Compound) | $10^{-4}$ | 1 |

*Compared in the concentration where the compound showed a relaxation rate of 15.7%

TABLE 3

$EC_{50}$ and maximum relaxation rate of the test drug in the antagonism test to contraction by potassium chloride

| Test Drug | $EC_{50}$ (M) | Maximum Relaxation Rate (%) |
|---|---|---|
| Compound A (Active Ingredient of the Present Invention) | $1.1 \times 10^{-5}$ | 69.1 |
| CGP-12, 177A (Control Compound) | $>10^{-4}$ | 17.4 |

TABLE 4

Concentration comparison of the compound A expressing the maximum relaxation rate of CGP-12, 177A in antagonism test to contraction by potassium chloride

| Test Drug | Concentration (M) | Comparison of Action Strength* |
|---|---|---|
| Compound A (Active Ingredient of the Present Invention) | $2.6 \times 10^{-7}$ | 383 |
| CGP-12, 177A (Control Compound) | $10^{-4}$ | 1 |

*Compared in the concentration where the compound showed a relaxation rate of 17.4%

Example 2

Rat Rhythmic Bladder Contraction Measurement Test

Test Method

The test was conducted by referring to *European Journal of Pharmacology*, 2000, volume 407, page 175.

1. Measuring Method

Female rats (225 to 290 g) of Wistar strain was used for the test. Under anesthetization with urethane, right and left ureters were ligated and cut and, after that, a polyethylene cannula was inserted from external urinary meatus and fixed. One end of the fixed cannula was connected to a pressure transducer via a three-way cock and pressure in the bladder was measured. Another end thereof was connected to a syringe pump and a physiological saline solution was continuously infused at a constant rate into bladder whereupon rhythmic bladder contraction was induced. The continuous infusion of a physiological saline solution was stopped after a rhythmic bladder contraction was noted. After the rhythmic bladder contraction was stabilized, drug or vehicle was administered from a catheter for administration of drug inserted into femoral vein.

2. Drug

The compound A was intravenously administered in increased doses where the ratio was 3 (0.03, 0.1, 0.3, 1 and 3 mg/kg). A group to which vehicle was administered was used as a control group.

3. Evaluated Items and Statistical Analysis

Parameters for evaluation were number of times and contraction pressure of bladder contraction during 10 minutes from 5 to 15 minutes after the administration of the drug and each group was conducted in n=5. The result is shown in terms of mean value±standard error and Student t-test was conducted for comparison between the two groups.

Results

By intravenous administration of the compound A, contraction frequency of rhythmic bladder contraction decreased on a dose-dependent manner (FIG. 3). An action of decreasing the contraction frequency by intravenous injection (i.v.) of 3 mg/kg of the compound A was significant as compared with the control group. On the other hand, the compound A did not affect the contraction pressure until intravenous administration of 3 mg/kg (FIG. 4). The fact of no influence on the contraction pressure is a preferred property from the viewpoint that urinary retention is not induced or that residual urine is not resulted upon urination.

A suppressive effect for contraction frequency by the compound A is presumed to be due to an increase in bladder volume by stimulation of the compound A for a $\beta_3$ receptor existing in the bladder. It has been believed that an increase in functional bladder volume showing the urine volume which is able to be stored in the bladder is clinically useful for the treatment of patients suffering from overactive bladder and, therefore, the compound A is believed to be clinically effective as a remedy for overactive bladder.

Example 3

Test for Measurement of Urination Function of Model Rat Suffering from Overactive Bladder Induced by Cyclophosphamide Overactive bladder model rats induced by cyclophosphamide were prepared by referring to *British Journal of Pharmacology*, 2000, volume 130, page 331 and the following test was conducted.

Test Method

1. Measuring Method

Female rats (220 to 230 g) of Wistar strain were used for the test. Under anesthetization with pentobarbital sodium, a catheter for infusion of physiological saline solution and for measurement of pressure in bladder was inserted into bladder from the top of the bladder and fixed while a catheter for administration of a drug was inserted into carotid vein and fixed. Cyclophosphamide (CYP) was administered into abdominal cavity and, after being recovered, the rats were returned to a feeding cage. On the next day of the operation, one end of the catheter inserted into bladder of the rat was connected to a syringe pump via a three-way cock and a physiological saline solution was continuously infused whereby |micturition| reflex was induced. Another end was connected to a pressure transducer and pressure in the bladder was measured. After the micturition reflex was stabilized, 1 mg/kg of the compound A was administered from a catheter for administration of drug which was inserted into carotid vein.

2. Evaluated Items and Statistical Analysis

Parameter for the evaluation was an average interval for urination from administration of the drug until 30 minutes thereafter. The result was shown in terms of an average urination interval after administration of the drug to the average urination interval before administration of the drug where an average urination interval during 30 minutes before administration of the drug was defined 1000 and was shown in a mean value of n=3.

Results

As a result of intravenous administration of the compound A (1 mg/kg), micturition interval of overactive bladder model rats induced by cyclophosphamide was elongated to an extent of 17.3% (FIG. 5). From such a fact, the compound A which prolongs the micturition interval of the present model rats is believed to be clinically effective as a remedy for overactive bladder.

Thus, the active ingredient of the present invention shows a strong bladder relaxation action in "isolated rat bladder smooth muscle relaxation test", decreases the contraction frequency of rhythmic bladder contraction on a dose-depending manner in "rat rhythmic bladder contraction measurement test" and prolongs the micturition interval in "micturition function measurement test on cyclophosphamide-induced overactive bladder model rat" whereby it is clinically useful as a remedy for overactive bladder. In addition to overactive bladder as a result of benign prostatic hyperplasia, it is also able to be used as a remedy for overactive bladder accompanied with urinary urgency, urinary incontinence and pollakiuria.

Example 4

Formulation Example

Formulation Example for Oral Agent

TABLE 5

| Composition | |
|---|---|
| Tablet | |
| Active ingredient of the present invention | 100.0 mg |
| Lactose | 199.5 mg |
| Corn starch | 40.0 mg |
| Hydroxypropyl cellulose | 9.0 mg |
| Magnesium stearate | 1.5 mg |
| Subtotal | 350 mg |
| Coat | |
| Hydroxypropyl methyl cellulose 2910 | 8.7 mg |
| Polyethylene glycol 6000 | 1.2 mg |
| Titanium oxide | 4.8 mg |
| Talc | 0.3 mg |
| Subtotal | 15 mg |
| Grand total | 365 mg |

100-mg Tablet

The active ingredient of the present invention (200.0 g) and 399.0 g of lactose were mixed in a polyethylene bag. The mixture was mixed and disintegrated in a sample mill (manufactured by Hosokawa Micron). The disintegrated mixture (450.0 g) and 60.1 g of corn starch were uniformly mixed in a fluidized granulation coating apparatus (manufactured by Ogawara Seisakusho). A 10% hydroxypropyl cellulose solution (192 g) was sprayed thereon to granulate. After being dried, the above was passed through a sieve of 20 meshes, 2.3 g of magnesium stearate was added thereto and the mixture was made into tablets each comprising 350 mg by a rotary tabletting machine (manufactured by Hata Tekkosho) using a pounder of ¢9.0 mm×10.8 R. The tablets were sprayed with 150 g of a coating solution containing 8.7 g of hydroxypropyl methyl cellulose, 1.2 g of polyethylene glycol 6000, 4.8 g of titanium oxide and 0.3 g of talc in a coating apparatus (manufactured by Freund Sangyo) to give film-coated tablets each being coated with 15 mg.

INDUSTRIAL APPLICABILITY

As mentioned hereinabove, (R)-2-(2-aminothiazol-4-yl)-4'-[2-[(2-hydroxy-2-phenylethyl)amino]ethyl]acetic acid anilide or a salt thereof which is an active ingredient of the present invention showed a significantly strong relaxation action as compared with the control compound in "isolated rat bladder smooth muscle relaxation test". Further, it decreased the contraction frequency of rhythmic bladder contraction on a dose-dependent manner in "rat rhythmic bladder contraction measurement test". Still further, it prolonged the micturition interval of cyclophosphamide-induced overactive bladder model rat in "micturition function measurement test on cyclophosphamide-induced overactive bladder model rat".

Accordingly, (R)-2-(2-Aminothiazol-4-yl)-4'-[2-[(2-hydroxy-2-phenylethyl)amino]ethyl]acetic acid anilide or a salt thereof which is an active ingredient of the present invention is able to be used as a remedy for overactive bladder. In addition to overactive bladder as a result of benign prostatic hyperplasia, it is also able to be used as a remedy for overactive bladder accompanied with urinary urgency, urinary incontinence and pollakiuria.

Figure 1:
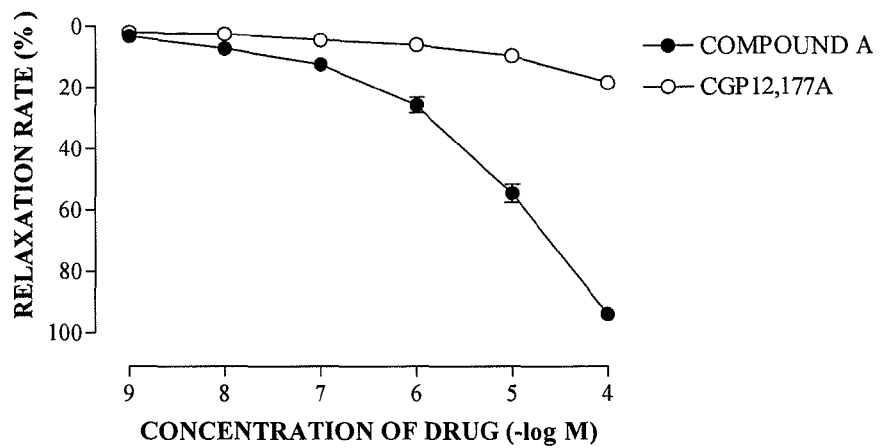
FIG. 1: Effects of the compound A and the control compound to isolated rat bladder smooth muscle relaxation test (antagonism test to contraction by carbachol)
Figure 2:
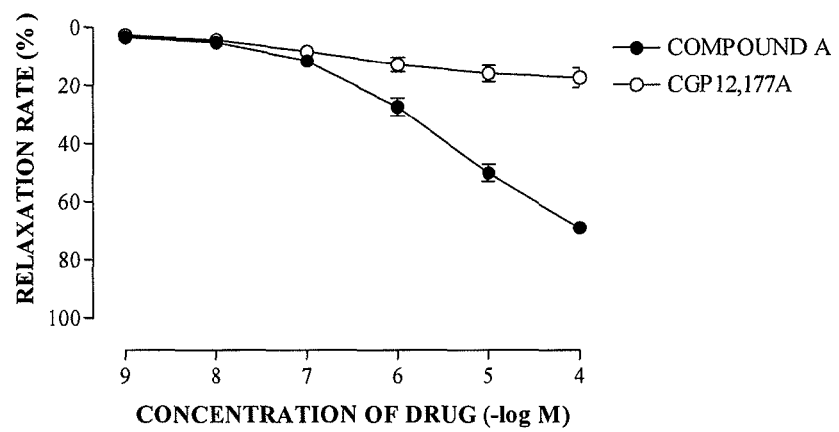
FIG. 2: Effects of the compound A and the control compound to isolated rat bladder smooth muscle relaxation test (antagonism test to contraction by potassium chloride)
Figure 3:
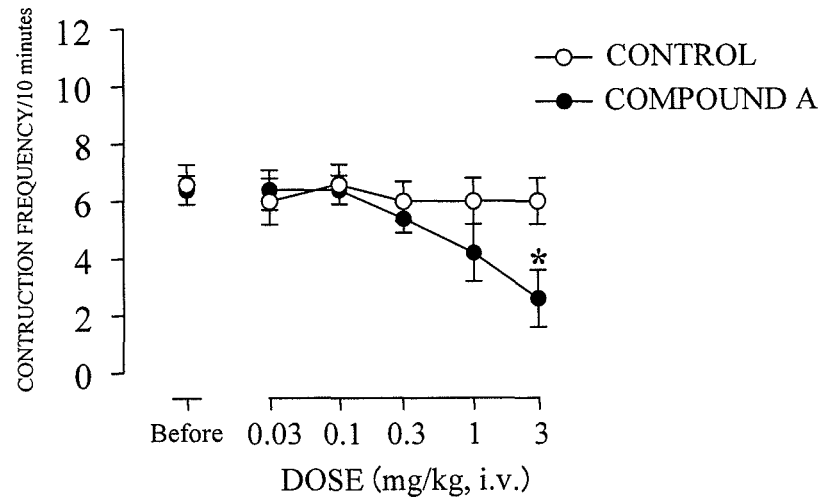
FIG. 3: Effect of the compound A to rat rhythmic bladder contraction (effect to contraction frequency (*: $p<0.05$))
Figure 4:
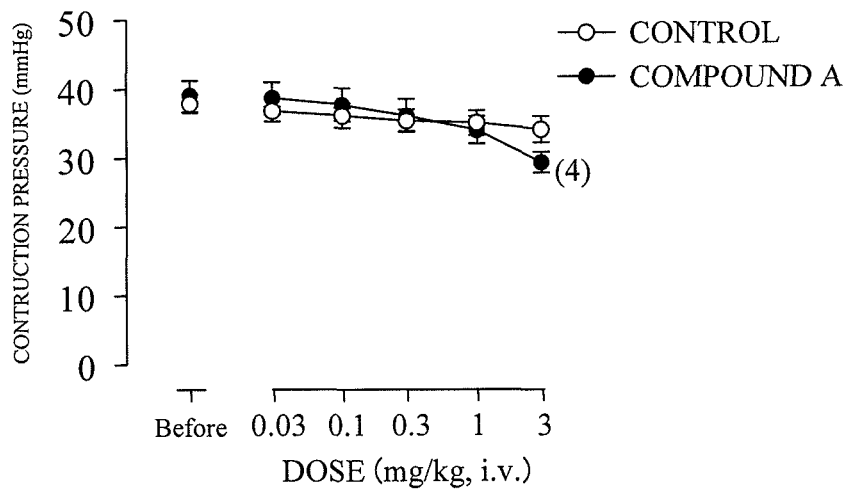
FIG. 4: Effect of the compound A to rat rhythmic bladder contraction (effect to contraction pressure)
Figure 5:
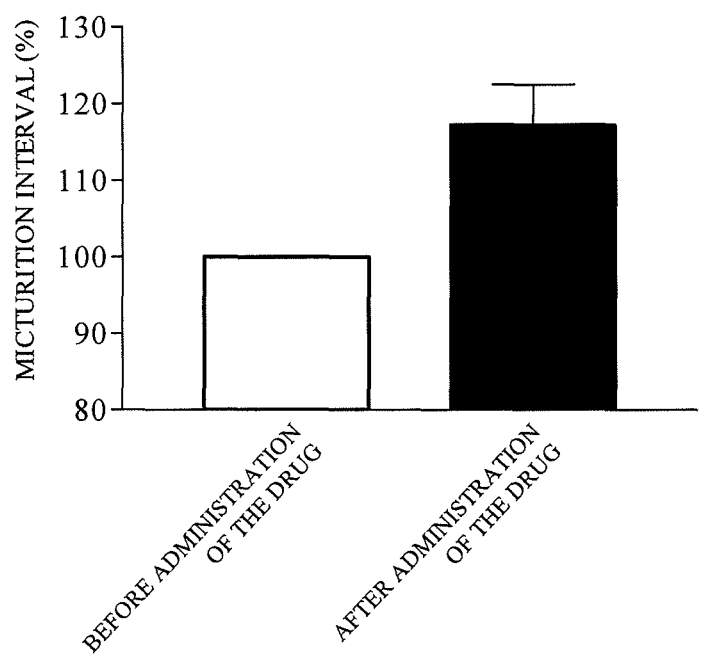
FIG. 5: Effect of the compound A to micturition function of cyclophosphamide-induced overactive bladder model rat (showing the urination interval after administration of a drug where the urination interval before administration of the drug was defined as 100%)

The invention claimed is:

1. A method for treating overactive bladder comprising administering an effective amount of (R)-2-(2-aminothiazol-4-yl)-4'-[2-[(2-hydroxy-2-phenylethyl)amino]ethyl]acetic acid anilide or a salt thereof as an active ingredient to a subject in need thereof.

2. The method according to claim 1, wherein said overactive bladder is a result of benign prostatic hyperplasia.

3. The method according to claim 1, wherein said subject has urinary urgency.

4. The method according to claim 1, wherein said subject has urinary incontinence.

5. The method according to claim 1, wherein said subject has pollakiuria.

6. The method according to claim 1, wherein (R)-2-(2-aminothiazol-4-yl)-4'-[2-[(2-hydroxy-2-phenylethyl)amino]ethyl]acetic acid anilide or a salt thereof is administered orally.

7. A method for treating overactive bladder comprising administering an effective amount of a free base of (R)-2-(2-aminothiazol-4-yl)-4'-[2-[(2-hydroxy-2-phenylethyl)amino]ethyl]acetic acid anilide as an active ingredient to a subject in need thereof.

8. The method according to claim 7, wherein said overactive bladder is a result of benign prostatic hyperplasia.

9. The method according to claim 7, wherein said subject has urinary urgency.

10. The method according to claim 7, wherein said subject has urinary incontinence.

11. The method according to claim 7, wherein said subject has pollakiuria.

12. The method according to claim 7, wherein the free base of (R)-2-(2-aminothiazol-4-yl)-4'-[2-[(2-hydroxy-2-phenylethyl)amino]ethyl]acetic acid anilide is administered orally.

* * * * *